(12) United States Patent
Grant et al.

(10) Patent No.: US 8,216,212 B2
(45) Date of Patent: Jul. 10, 2012

(54) PROVIDING HAPTIC FEEDBACK TO THE HANDLE OF A TOOL

(75) Inventors: Danny A. Grant, Laval (CA); Christopher J. Ullrich, Santa Cruz, CA (US); Juan Manuel Cruz-Hernandez, Montreal (CA); Christophe Ramstein, San Francisco, CA (US)

(73) Assignee: Immersion Corporation, San Jose, CA (US)

( * ) Notice: Subject to any disclaimer, the term of this patent is extended or adjusted under 35 U.S.C. 154(b) by 336 days.

(21) Appl. No.: 12/354,302

(22) Filed: Jan. 15, 2009

(65) Prior Publication Data

US 2010/0179587 A1    Jul. 15, 2010

(51) Int. Cl.
*A61B 17/00* (2006.01)
(52) U.S. Cl. .......................................................... 606/1
(58) Field of Classification Search .............. 606/1, 205; 251/65; 600/587
See application file for complete search history.

(56) References Cited

U.S. PATENT DOCUMENTS

| 5,389,849 A | 2/1995 | Asano et al. |
| 5,609,607 A * | 3/1997 | Hechtenberg et al. ........ 606/205 |
| 2001/0025150 A1 | 9/2001 | de Juan, Jr. et al. |
| 2002/0120188 A1 | 8/2002 | Brock et al. |

FOREIGN PATENT DOCUMENTS

| CA | 2520942 A1 | 3/2007 |
| WO | WO-00/51486 | 9/2000 |
| WO | WO-01/91100 A1 | 11/2001 |
| WO | WO-03/020139 A2 | 3/2003 |

OTHER PUBLICATIONS

International Search Report, Int'l Appl No. PCT/US2010/020010 Mar. 18, 2010.

* cited by examiner

*Primary Examiner* — Brian Szmal
(74) *Attorney, Agent, or Firm* — Medler Ferro PLLC

(57) ABSTRACT

Tools, such as surgical tools, are normally designed to interact with an object, such as a patient. As disclosed herein, one particular tool is implemented such that it comprises a handle having a feedback portion configured to contact one or more digits of a user's hand. The tool also includes a sensor positioned near or in contact with an object. The sensor is configured to measure a property of the object. Also, the tool includes a haptic output mechanism supported by the feedback portion of the handle. The haptic output mechanism is configured to communicate the measured property of the object to the user.

12 Claims, 4 Drawing Sheets

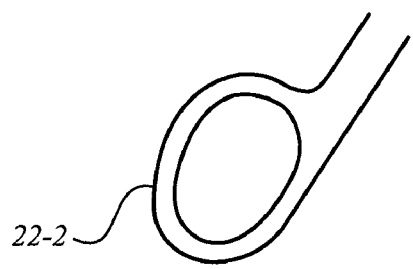
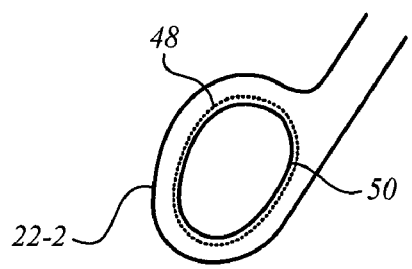
FIG. 7A  FIG. 7B
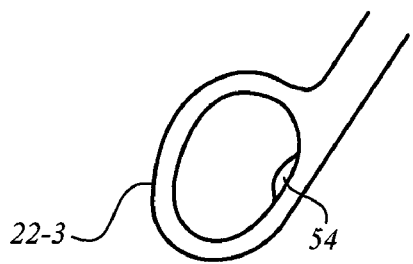
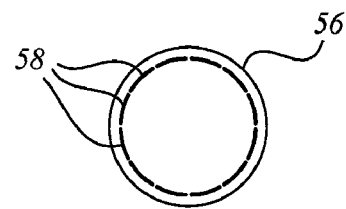
FIG. 8  FIG. 9
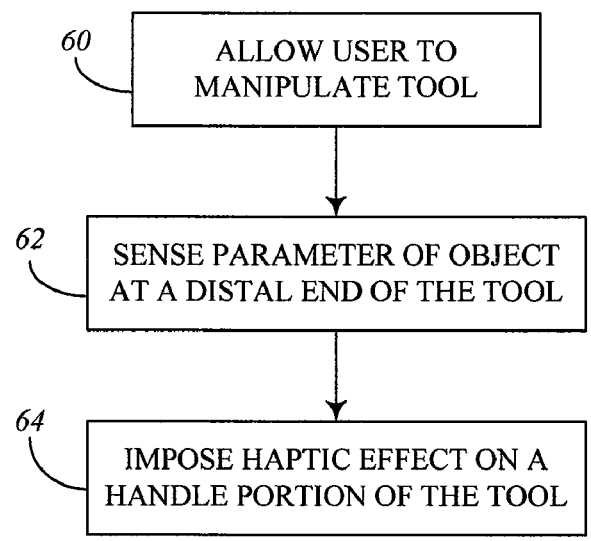
FIG. 10

PROVIDING HAPTIC FEEDBACK TO THE HANDLE OF A TOOL

TECHNICAL FIELD

The present disclosure generally relates to embodiments of hand tools. More particularly, the present disclosure relates to sensing a property of an object and providing haptic feedback to one or more haptic actuating devices mounted on a handle of the tool.

BACKGROUND

As opposed to open surgery in which a surgeon cuts a relatively large incision in the skin of a patient for accessing internal organs, minimally invasive surgical procedures are performed by making relatively small incisions and then inserting tools through the incisions to access the organs. Minimally invasive surgery usually results in shorter hospitalization times, reduced therapy requirements, less pain, less scarring, fewer complications, etc.

During minimally invasive surgery, the surgeon can introduce a miniature camera through an incision. The camera transmits images to a visual display, allowing the surgeon to see the internal organs and tissues and to see the effect of other minimally invasive tools on the organs and tissues. In this way, the surgeon is able to perform laparoscopic surgery, dissection, cauterization, endoscopy, telesurgery, etc. Compared to open surgery, however, minimally invasive surgery can present limitations regarding the surgeon's ability to see and feel the patient's organs and tissues.

SUMMARY

The present disclosure describes a number of embodiments of tools for communicating sensed parameters to an operator of the tool. In accordance with one particular embodiment, among others, a tool described herein comprises a handle having a feedback portion configured to contact one or more digits of a user's hand. The tool further includes a sensor, which is positioned near or in contact with an object and is configured to measure a property of the object. Also, the tool includes a haptic output mechanism supported by the feedback portion of the handle. The haptic output mechanism is configured to communicate the measured property of the object to the user.

The embodiments described in the present disclosure may include additional features and advantages, which may not necessarily be expressly disclosed herein but will be apparent to one of ordinary skill in the art upon examination of the following detailed description and accompanying drawings. It is intended that these additional features and advantages be included within the present disclosure.

BRIEF DESCRIPTION OF THE DRAWINGS

The components of the following figures are illustrated to emphasize the general principles of the present disclosure and are not necessarily drawn to scale. Reference characters designating corresponding components are repeated as necessary throughout the figures for the sake of consistency and clarity.

FIGS. 7A and 7B are diagrams illustrating a side view of part of the handle shown in FIG. 1, according to a second embodiment.

FIG. 8 is a diagram illustrating a side view of part of the handle shown in FIG. 1, according to a third embodiment.

FIG. 9 is a diagram illustrating a cross-sectional side view of a handle, according to another embodiment.

FIG. 10 is a flow diagram illustrating a method of operation of a tool, according to one embodiment.

DETAILED DESCRIPTION

Although minimally invasive surgical procedures involving small incisions include many advantages over open surgery, minimally invasive surgery can still create challenges to a surgeon. For example, the surgeon must typically rely on a camera to view the patient's internal organs and see how the movement and operation of the tools affects the organs. To enhance the surgeon's experience, however, feedback can be provided to the surgeon to communicate information about how the body of the patient reacts to the tools. According to the teachings of the present disclosure, output can be provided to the surgeon by imposing haptic effects on a section of the handle of the tool. Particularly, haptic effects can be imposed on a section of the tool intended to accommodate the surgeon's fingers or thumb.

The present disclosure describes many embodiments that may apply to any type of tool that can be manipulated by an operator. More particularly, the tools described in the present disclosure include a handle portion that mechanically controls a distal portion of the tool. Mounted on the distal portion are one or more sensors configured to sense a parameter of an object that interacts with the tool. The sensed signals can be processed to obtain output signals designed to be provided to one or more haptic output mechanisms mounted on the handle.

Although many of the examples described in the present disclosure relate to surgical tools, such as minimally invasive surgical tools, it should be understood that the present disclosure is intended to encompass other types of tools as well. In addition, although many of the examples herein relate to surgical patients and how the organs and tissues of the patients interact with the surgical tools, it should also be understood that the present disclosure also pertains to other types of objects that are intended to interact with or react to the operations of the respective tools. Other features and advantages of the tools will be apparent to one of ordinary skill in the art upon reading and understanding the general principles of the present disclosure. These implied features and advantages are also intended to be included herein.

Figure 1:
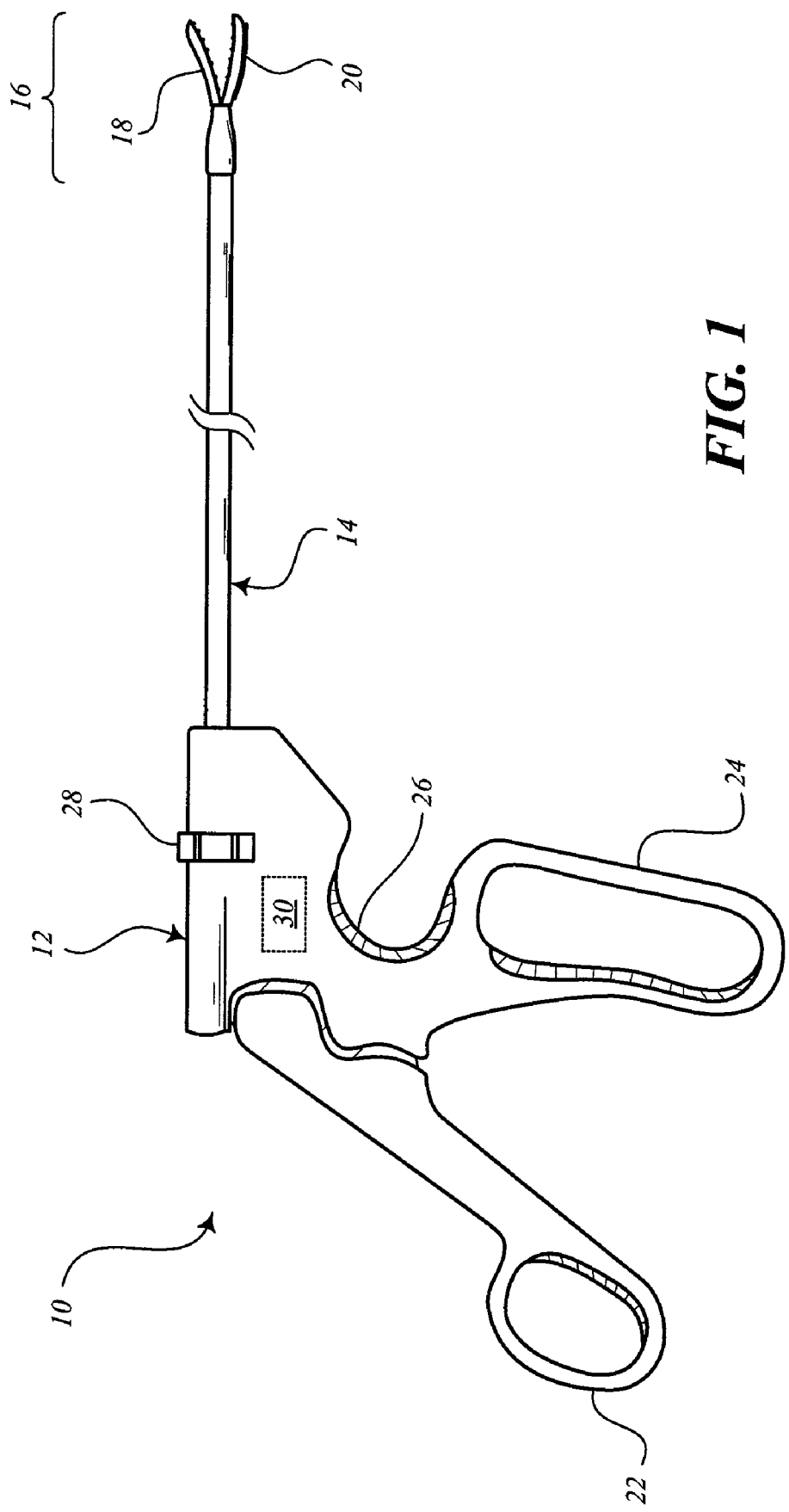
FIG. 1 is a diagram illustrating a side view of a surgical tool according to one embodiment.

FIG. 1 is a diagram illustrating an embodiment of a surgical tool 10. In this diagram, surgical tool 10 is shown as a laparoscopic tool, one end of which is configured to be inserted through a small incision in the abdomen of a patient. Surgical tool 10 in this embodiment includes a handle 12, a shaft 14, and a distal portion 16. Shaft 14 is designed to connect handle 12 to distal portion 16 and to communicate any mechanical actions of handle 12 to distal portion 16. Shaft 14 is further designed to communicate electrical signals from distal portion 16 back to handle 12 as explained in more detail below.

According to the embodiment of FIG. 1, distal portion 16 includes a tip 18 and a sensing device 20 formed on tip 18. As illustrated in FIG. 1, tip 18 is a grasper and sensing device 20 is connected to a bottom jaw of the grasper. However, it should be understood that surgical tool 10 may include any suitable type of tip having any suitable functionality. Also, sensing device 20 may be connected to any portion or portions of the respective tip. In some embodiments, tip 18 may be omitted and sensing device 20 may be mounted on another portion of distal portion 16 to perform its intended sensing functionality. In this respect, surgical tool 10 can be embodied as a sensing device for the sole purpose of sensing one or more signals at distal portion 16. According to some examples of the embodiment of FIG. 1, shaft 14 may be about 20 cm to 30 cm in length and tip 18 may be about 10 mm to 15 mm in length.

By manipulating handle 12, an operator can insert distal portion 16 into the abdomen of the patient and control tip 18 of distal portion 16. When distal portion 16 is inserted, the surgeon can further manipulate handle 12 to control the location and orientation of tip 18 such that sensing device 20 is able to contact certain regions of the patient. Sensing device 20 may include one or more sensors each configured to measure or test any desired parameter of the patient, such as, for example, pulse, stiffness, etc. In some embodiments in which sensing device 20 does not necessarily need to contact a particular region of the patient, tip 18 can be controlled to position sensing device 20 to accomplish certain contactless sensing functions.

Sensing device 20 can be configured to sense any suitable property of the object under test. For instance, sensing device 20 can be configured as pressure sensors using resistive or capacitive pressure sensing technologies. Alternatively, sensing device 20 can include strain gauges, piezoelectric sensors, stiffness sensors, etc. As strain gauges, sensing device 20 can provide additional information about contact force and can be configured to finely tune a generally course measurement of force. As piezoelectric sensors, sensing devices 20 can include a transmission device to generate ultrasound signals that reflect off portions of the object. In this case, echo signals can be detected by sensing device 20 to determine the location of objects. Sensing device 20 can also be configured as stiffness sensors that can detect nodules, e.g., tumors, or other stiff regions of the patient.

In the embodiment of FIG. 1, handle 12 of surgical tool 10 includes a receptacle 22, which is designed to accommodate the thumb of the surgeon's hand. Handle 12 also includes a second receptacle 26, which accommodates the lower three fingers of the surgeon's hand, and a recess 26 designed to accommodate the index finger of the surgeon's hand. In many of the embodiments described in the present disclosure, the receptacle for the surgeon's thumb, e.g., receptacle 22, is described in detail. However, it should be noted that similar features can be implemented for other receptacles and recesses designed for other digits or other parts of the operator's hand or hands. In this respect, the features of the receptacles can be embodied in any portion of the handle.

One or more haptic actuating devices can be incorporated in receptacle 22 to impose haptic effects on the surgeon's thumb. In other embodiments, one or more haptic actuating devices can be incorporated in other parts of handle 12, such as in receptacle 24 and recess 26, to impose haptic effects on other parts of the surgeon's fingers and hand. Signals sensed by sensing device 20 can be processed as needed and applied to the haptic actuating devices to communicate the sensed signals to the surgeon. Receptacle 22 can be generally configured to surround the surgeon's thumb in order that output signals can be communicated to different sides of the thumb. If necessary, an adapter or supplemental material may be placed on the inside surfaces of receptacle 22 to properly contact multiple points around the surgeon's thumb. This adapter can be used, for example, to account for different sizes of thumbs of various users.

Handle 12 may also include a processing device 30, which may be positioned inside a housing of handle 12. Processing device 30 is configured to process the signals from sensing device 20 and control the output signals provided to the one or more haptic actuating devices formed in receptacle 22. Processing device 30, for example, may be a general-purpose or specific-purpose processor or microcontroller. In some embodiments, processing device 30 may be associated with a memory device for storing data and/or instructions. Logical instructions, commands, and/or code can be implemented in software, firmware, or both, and stored in the memory device. In other embodiments, logical instructions, commands, and/or code can be implemented in hardware and incorporated in processing device 30 using discrete logic circuitry, an application specific integrated circuit ("ASIC"), a programmable gate array ("PGA"), a field programmable gate array ("FPGA"), etc., or any combination thereof. Depending on the type of sensing mechanisms that may be used in relation to sensing device 20 and the type of properties being measured, the algorithms of processing device 30 can determine various characteristics of the object.

The haptic actuating devices located in receptacle 22 may be configured to provide feedback signals based on signals sensed at distal portion 16 of surgical tool 10 and processed by processing device 30. The haptic actuating devices may include electromagnetic motors, electro-active polymers or other materials that deform or change shape in response to signals, materials or mechanisms for changing stiffness, vibrotactile actuators, inertial actuators, piezoelectric actuators, etc. In one example, the haptic actuating devices may comprise a grasping characteristic can be used to convey contact force, pressure, etc.

Furthermore, handle 12 includes a rotary device 28, which can be used as a "roll" control device. Rotary device 28 can be directly or indirectly connected to shaft 14 and is configured to rotate shaft 14 about its axis. When the operator rotates rotary device 28, shaft 14 and distal portion 16 rotate in a corresponding manner. Thus, the operator can control the rotational orientation of tip 18 and sensing device 20. In a sensing mode, the operator can direct sensing device 20 in a desired orientation to obtain sensor signals of certain regions of the patient. In one example, sensing device 20 can be mounted such that it faces away from shaft 14 or distal portion 16 in a direction substantially perpendicular to the axis of shaft 14. By rotating rotary device 28 to control the roll, sensing device 20 can sweep around the axis to observe the surrounding tissue in order to identify vasculature, tumor masses, etc., using a visual sensor, stiffness sensor, or other suitable type of sensor.

Figure 2:
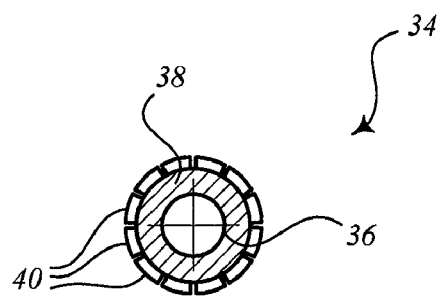
FIG. 2 is a diagram illustrating a cross-sectional view of a set of sensors mounted on a tool, according to one embodiment.

FIG. 2 is a cross-sectional view showing an embodiment of a sensor 34 mounted on a shaft 36 of a tool. Shaft 36 may be configured to connect a handle portion of the tool with a distal portion, where the distal portion may include one or more functional elements. In some embodiments, shaft 36 may correspond to shaft 14 shown in FIG. 1. Sensor 34 may be mounted on a distal end of shaft 36 or along any portion of shaft 36. In some embodiments, sensor 34 may be mounted on a portion of a tip located at the distal end of the tool.

According to the embodiment of FIG. 2, sensor 34 includes a support device 38 and a plurality of sensing elements 40 arranged circumferentially around support device 38. Each one of sensing elements 40 may be oriented in a direction facing away from shaft 36, wherein each sensing element 34 faces in a different angular direction. In this respect, it is possible for sensing elements 40 to sense the surrounding areas of the patient simultaneously. It should be recognized that sensing elements 40 may include any suitable type of sensors and functionality, such as is mentioned above with respect to sensing element 20. Sensor 34 may include any number of sensing elements 40 and may be positioned and oriented in any suitable location, direction, or angle. In some embodiments, sensing elements 40 may be mounted on support device 38 in a predetermined pattern according to a specific design.

In some embodiments, the number of sensing elements 40 may correspond to the number of haptic actuating devices positioned in a receptacle or recess of a handle of a tool. For example, sensing elements 40 may be directly correlated with the haptic actuating devices located in receptacle 22 shown in FIG. 1 or with another set of actuating devices. Particularly, the actuating devices may be arranged in a manner corresponding to the manner in which sensing elements 40 are arranged, or vice versa. According to the embodiments illustrated herein, sensing elements 40 can be formed or supported in a substantially circular arrangement. In addition, when the actuating devices and sensing elements 40 are arranged in a similar manner, each actuating device can be matched with a corresponding sensing element 34. Thus, one actuating device can be designed to provide feedback based on the signals sensed by a corresponding sensing element 34 located in the same respective position of the arrangement. Sensor 34 is configured to measure one or more properties of the patient, which interacts or reacts with the surgical tool that supports sensor 34.

Figure 3:
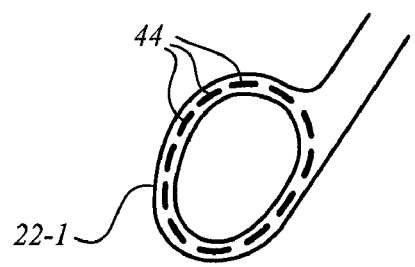
FIG. 3 is a diagram illustrating a cross-sectional side view of part of the handle shown in FIG. 1, according to a first embodiment.

FIG. 3 is a cross-sectional side view showing a first embodiment of a receptacle 22-1, which is part of a handle of a tool. In particular, receptacle 22-1 is a feedback portion of the handle. Receptacle 22-1 may correspond, for example, to a possible embodiment of receptacle 22 of surgical tool 10 shown in FIG. 1. In this embodiment, receptacle 22-1 includes a plurality of haptic actuating devices 44. Particularly, the number of haptic actuating devices 44 in this embodiment is twelve, which corresponds to the same number of sensing elements 40 shown in FIG. 2. However, it should be noted that the numbers of haptic actuating devices 44 and sensing elements 40 may be the same, different, multiples, etc.

Haptic actuating devices 44 are supported by the material of receptacle 22-1 in any suitable manner. Haptic actuating devices 44 are configured to communicate a property of the patient measured by a corresponding group of sensing element. Haptic actuating devices 44 impose haptic effects on the user of the tool. More specifically, receptacle 22-1 may be configured to accommodate the thumb of one of the user's hands.

Haptic actuating devices 44 may be distributed throughout receptacle 22-1. As illustrated, haptic actuating devices 44 are arranged in a substantially circular configuration. Each haptic actuating device 38 may be configured to correspond to a respective sensing element, such as sensing elements 40 (FIG. 2), for imposing a haptic effect based on the signals sensed at the respect sensing element. One or more of haptic actuating devices 44 may be positioned in particular locations in receptacle 22-1 and actuated based on the sensed property of a respective sensing element corresponding to the location of the sensing elements with respect to the shaft.

In another implementation, each haptic actuating device 38 may be configured to correspond to a particular direction in which a single sensor, such as sensing device 20 (FIG. 1), is oriented. Referring to another embodiment, one or more sensors can be mounted on a grasper, and haptic actuating devices 44 may be configured to communicate the position of a portion of the object with respect to a jaw of the grasper. In this respect, if only a small portion of the object is within the jaws of the grasper, then only a small number of haptic actuating devices 44 are activated.

Figure 4A:
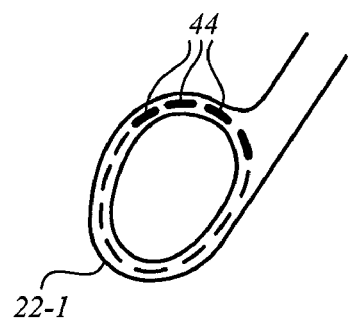
FIGS. 4A-4C are diagrams illustrating the activation of the haptic actuating devices shown in FIG. 3 according to a first implementation.
Figure 4B:
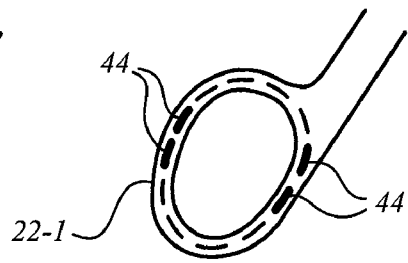
Figure 4C:
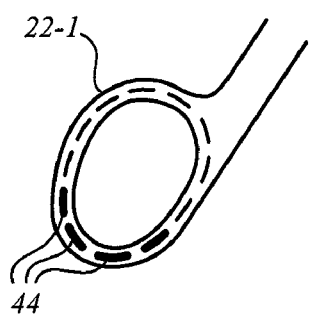

FIGS. 4A-4C are diagrams illustrating the activation of haptic actuating devices 44 shown in FIG. 3 according to a first implementation. In this embodiment, haptic actuating devices 44 are designed to communicate directionality information to the user. For example, processing device 30 shown in FIG. 1 may be configured to control haptic actuating devices 44 to convey information concerning directionality. In one implementation, the directionality information may represent the orientation of the tip of the tool, which can be controlled by physically turning the entire tool or by rotating a rotary device, such as rotary device 28. In addition, directionality information may represent the location that a sensor contacts the object, e.g., patient. In some cases, the direction of a sensed parameter can vary with time. For example, a pulse may be detected in a first direction or at a first location at one time and then in a second direction or at a second location immediately thereafter.

Regarding FIG. 4A, haptic actuating devices 44 that are located near a top portion of receptacle 22-1 are activated to correspond to sensor information related to a top portion of one or more sensors, an upper portion of the tool, an upward orientation, etc. With respect to one example, a single sensor at the distal end of a tool can sense a property, e.g., stiffness, of the patient when that sensor is directed or oriented in an upward direction. With respect to another example, a set of sensors formed around a distal end of a tool can be used, such that the sensors positioned in a top region sense a particular parameter, e.g., stiffness, or senses when a property at the top region reaches a specific level.

Concerning FIG. 4B, haptic actuating devices 44 that are located near one or both of the sides of receptacle 22-1 are activated. The activation of these actuating devices 32 may correspond, for example, to sensor information of the patient received from a left or right region of the distal end of the tool. For instance, if a single sensor is used, the activation of the side positioned haptic actuating devices 44 may correspond to the sensor being oriented or directed to the side. As illustrated in FIG. 4B, haptic actuating devices 44 on both the left and right side are activated simultaneously. However, it should be recognized that haptic actuating devices 44 on only the right side or left side may be activated at a time, representing a specific feature at the right or left side of the distal end. In the case where multiple sensors are used at the distal end of the tool, activation of haptic actuating devices 44 on the sides may correspond to specific signals being sensed at the corresponding sensors.

With respect to FIG. 4C, haptic actuating devices 44 that are located near the bottom of receptacle 22-1 are activated. The activation of the bottom haptic actuating devices 44 may correspond, for example, to sensor information of the patient received from a bottom region of the distal end of the tool. For a single sensor, the detection of specific signals when the orientation of the sensor is in a downward direction can cause the activation of the bottom haptic actuation devices 32. Alternatively, when multiple sensors are used, the detection of specific signals from the bottom positioned or bottom directed sensors can cause the activation of the bottom haptic actuation devices 32.

Haptic actuating devices 44 shown in FIGS. 4A-4C can also be actuated to indicate the direction or orientation of an end portion relative to a center shaft. For example, the end portion may comprise an articulated grasper that can move with respect to the center shaft. Those haptic actuating devices 44 which are located at corresponding areas around the periphery can then be actuated to indicate the orientation of the head of the articulated grasper.

Figure 5A:
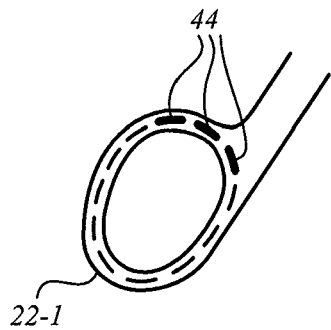
FIGS. 5A-5C are diagrams illustrating the activation of the haptic actuating devices shown in FIG. 3 according to a second implementation.
Figure 5B:
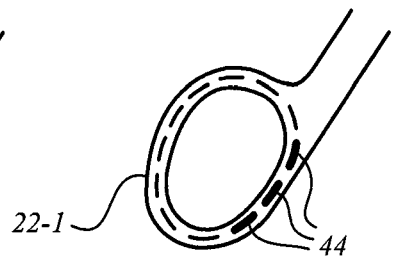
Figure 5C:
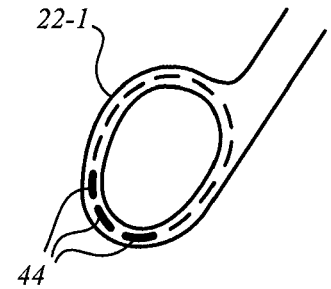

FIGS. 5A-5C are diagrams illustrating the activation of the haptic actuating devices 44 shown in FIG. 3 according to a second implementation. Haptic actuating devices 44 in this embodiment are designed to communicate any suitable type of information in a rotational fashion. For example, haptic actuating devices 44 may be activated to indicate flow, such as blood flow through a blood vessel. Alternatively, haptic actuating devices 44 may be activated to indicate a structure, such as tubular structure.

These three figures show the activation of certain haptic actuating devices 44 at subsequent times. As shown in this example, some haptic actuating devices 44 located near the top of receptacle 22-1 are activated at one time. At a later time, the side haptic actuating devices 44 are activated. Then, the bottom haptic actuating devices 44 are activated. In this sense, a clockwise activation sequence is applied. In other embodiments, haptic actuating devices 44 may be activated in a counterclockwise fashion to communicate any relevant characteristic of the object. The pattern of activation can be used to indicate any parameter or feature of the patient. For example, the activation sequence may be used to communicate the sensing of a pulse.

Figure 6A:
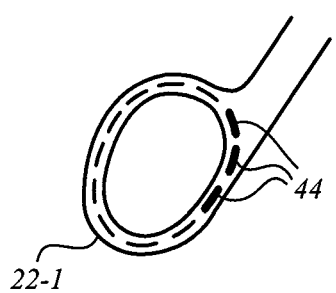
FIGS. 6A-6C are diagrams illustrating the activation of the haptic actuating devices shown in FIG. 3 according to a third implementation.
Figure 6B:
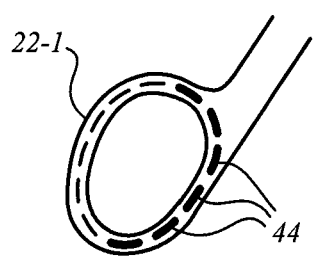
Figure 6C:
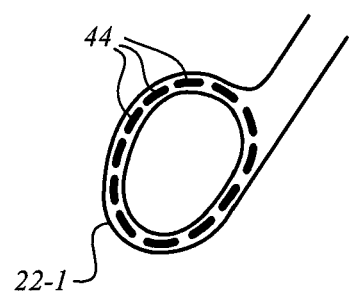

FIGS. 6A-6C are diagrams illustrating the activation of the haptic actuating devices 44 shown in FIG. 3 according to a third implementation. Haptic actuating devices 44 in this embodiment are configured to communicate positional information or spatial information relative to a position on the tool. In this case, multiple sensors may be positioned in an array or other predetermined pattern and used to sense a particular parameter.

These figures show possible activation of haptic actuating devices 44 to communicate, for example, the amount of an object that is held within the jaws of a grasper, gripper, or other similar type mechanism. In this case, FIG. 6A shows an example of activation of a small number of haptic actuating devices 44 when just a small portion of the object is held in the jaws. FIG. 6B shows an example of activation of a greater number of haptic actuating devices 44 when a larger amount of the object is within the grasp of the tool, e.g., about halfway in the tool's grasp. FIG. 6C shows an example of activation of all or nearly all haptic actuating devices 44 of receptacle 22-1 when the tool has a complete grasp of the object. This may be particularly useful when a procedure is being performed on the patient's colon, such as during a colonoscopy. Since too much force can tear the colon, which can cause severe complications, it is important that the colon is handle with sensitivity. In this respect, haptic actuating devices 44 can communicate to the surgeon the type of grasp that is being applied to the patient's colon. Other delicate organs may also require a certain level of sensitivity as well.

FIG. 7 is a side view showing a second embodiment of a receptacle 22-2, which is feedback portion of a handle of a tool. For example, receptacle 22-2 may correspond to one possible embodiment of receptacle 22 of surgical tool 10 shown in FIG. 1. In this embodiment, receptacle 22-2 includes a material that is configured to expand and contract in response to a signal related to a measured property of the object being tested. For example, in order to communicate a gripping force or other type of force on the object, the material of receptacle 22-2 may expand accordingly, thereby applying a force on all sides of the operator's thumb. In this case, the force applied to the user's hand can provide a more natural feeling to convey pressure sensed at the distal end of the tool, representing the pressure applied to the patient. Also, a force feedback type output may provide the advantage of simulating a similar measurement of pressure and can be less distracting to the user than a vibrotactile sensation.

FIG. 7A shows receptacle 22-2 in a contracted state, such as when no relevant signal is being sensed. In FIG. 7B, however, receptacle 22-2 is shown in an expanded state, wherein the material expands from a normal position 48 to an expanded position 50. The material may be configured to return to its normal position 48 when the signal is no longer sensed, after a short period of time, or after some other specific event. In some embodiments, the material capable of expanding and contracting may be used in other portions of the respective handle to apply pressure or force on other parts of the operator's hand.

FIG. 8 is a side view showing a third embodiment of a receptacle 22-3, which is feedback portion of a handle of a tool. For example, receptacle 22-3 may correspond to one possible embodiment of receptacle 22 of surgical tool 10 shown in FIG. 1. In this embodiment, receptacle 22-3 includes a programmable protrusion 54. Programmable protrusion 54 may be configured to have any suitable size and shape for properly communicating information to the user without causing great discomfort. Programmable protrusion 54 can communicate any type of information to the user, such as, for example, directional information, rotational information, relative position of an object with respect to one or more sensors, etc. Programmable protrusion 54 is designed to protrude toward the center of receptacle 22-3 so as to press against the skin of the user's thumb with a slight force to provide a greater contact with the thumb for allowing better communication with the nerves of the thumb.

Programmable protrusion 54 may be configured to expand and contract to communicate specific conditions of the sensed signals. In some embodiments, programmable protrusion 54 may be configured to vibrate or impose another type of haptic effect on the user's thumb. Programmable protrusion 54, according to other embodiments, may be configured to change stiffness according to a sensed signal. In this case, programmable protrusion 54 may alter its stiffness based on a stiffness measurement made by the sensing elements in contact with the patient. Hence, the surgeon can receive an indication of stiffness to help identify organs and tissue.

In some embodiments, a plurality of protrusions, each of which can be similar to protrusion 54, are positioned around the inside surface of receptacle 22-3. Each protrusion can be actuated individually or in conjunction with some or all of the other protrusions. Thus, sensed signals can be processed in a way that includes the actuation of one or more of the protrusions. In this respect, the protrusions can be actuated in the manner discussed with respect to FIGS. 4-6 to indicate direction, orientation, flow, degree or stage of a relative condition, etc.

FIG. 9 is a cross-sectional side view diagram illustrating an embodiment of a feedback portion of a handle 56. In this embodiment, handle 56 includes a plurality of haptic actuating devices 58 positioned under the outer surface of handle 56. Regarding various arrangements, haptic actuating devices 58 can be positioned under the surface of handle 56, flush with the surface, on top of the surface, or in any combination thereof. In this regard, FIG. 9 is directed to embodiments where actuation is imposed on the user from an outer surface of handle 56. On the other hand, FIGS. 3-8 describes embodiments that are directed to haptic actuation being imposed on the user from an inside surface of a finger/thumb receptacle.

Handle 56 can be a part of any tool that is capable of imposing haptic feedback, and, in particular, a graspable tool where haptic actuation is applied from an outside surface of handle 56. The feedback portion of handle 56 can be incorporated into any type of tool or equipment, such as electric drills, electric screwdrivers, bicycle handle bars, motorcycle handle bars, tennis racquets, golf clubs, etc. Furthermore, when haptic actuating devices 58 are arranged around the perimeter of handle 56 as shown, they can be programmed to function in a manner similar to the actuation techniques described above with respect to FIGS. 4-6.

FIG. 10 is a flow diagram of an embodiment of a method of operation of a tool providing haptic feedback to its handle. As indicated in block 60, a user or operator is allowed to manipulate a tool according to a normal use of the tool. For example, the operator may manipulate a handle, buttons, or other feature on the tool to control a functional portion of the tool. The functional portion may be positioned, for instance, on an opposite end of the tool from the handle. The functional portion can be probed around to contact an object being tested or to be placed in proximity to the object being tested, depending on the particular type of parameter being measured.

As indicated in block 62, one or more properties of an object are sensed at a distal end of the tool. Particularly, the property or properties may be sensed by one or more sensing devices. The sensors may be positioned on or near the functional portion of the tool. The sensed properties can be processed as needed to obtain output signals to be applied to output mechanisms on the tool. Based on the properties sensed and the types of output mechanisms incorporated in the tool, output signals can be obtained for each individual output mechanism or for an entire set of output mechanisms, depending on the particular application.

As indicated in block 64, one or more haptic effects are imposed on a portion of a handle of the tool. In some embodiments, other output signals can be provided to the one or more other output mechanisms. According to block 64, however, the sensed signals are communicated to the operator in a haptic manner. The haptic effects may include haptic outputs, vibrotactile effect outputs, etc.

It should be understood that the routines, steps, processes, or operations described herein may represent any module or code sequence that can be implemented in software or firmware. In this regard, these modules and code sequences can include commands or instructions for executing the specific logical routines, steps, processes, or operations within physical components. It should further be understood that two or more of the routines, steps, processes, and/or operations described herein may be executed substantially simultaneously or in a different order than explicitly described, as would be understood by one of ordinary skill in the art.

The embodiments described herein represent a number of possible implementations and examples and are not intended to necessarily limit the present disclosure to any specific embodiment. Instead, various modifications can be made to these embodiments as would be understood by one of ordinary skill in the art. Any such modifications are intended to be included within the spirit and scope of the present disclosure and protected by the following claims.

We claim:

1. A tool comprising:
    a handle having a receptacle configured to contact one or more digits of a user's hand;
    a shaft connecting the handle to a distal end of the tool;
    a sensor positioned at a distal end of the tool and configured to measure a property of an object, wherein the sensor comprises a plurality of sensing elements each of which is oriented in a direction that faces away from the shaft with each sensing element facing in a different angular direction; and
    a plurality of haptic actuating devices distributed in the receptacle to at least partially surround the one or more digits of a user's hand positioned therein, the plurality of haptic actuating devices configured to be actuated based on the measured property to provide haptic feedback to the user,
    wherein the plurality of haptic actuating devices are arranged in the receptacle in a manner corresponding to a manner in which the plurality of sensing elements are arranged such that each haptic actuating device is matched with a correspondingly located sensing element to be activated based on the sensed property of the correspondingly located sensing element.

2. The tool of claim 1, wherein the plurality of haptic actuating devices are arranged in the receptacle to surround the one or more digits of a user's hand positioned therein.

3. The tool of claim 1, wherein one or more of the haptic actuating devices positioned in the receptacle are activated based in part on a direction that the correspondingly located sensing element is oriented.

4. The tool of claim 1, wherein the plurality of sensing elements are mounted on a grasper, and one or more of the haptic actuating devices are configured to be activated to communicate a position of a portion of the object with respect to a jaw of the grasper.

5. The tool of claim 1, wherein the plurality of haptic actuating devices are arranged around an inside surface of the receptacle.

6. The tool of claim 5, wherein the receptacle is configured to accommodate the user's thumb, and wherein the plurality of haptic actuating devices are configured to communicate the measured property to the user's thumb while the thumb is positioned within the receptacle.

7. The tool of claim 1, wherein the receptacle is configured to be grasped by the user's hand and/or digits of the user's hand, and wherein the plurality of haptic actuating devices are arranged around an outside surface of the receptacle.

8. The tool of claim 1, wherein the tool is a surgical tool and the object is a patient.

9. A surgical tool comprising:
    means for sensing a property of a patient at a distal end of the surgical tool;
    means for imposing a haptic effect on a handle portion of the surgical tool in response to the sensed property, the imposing means configured to impose the haptic effect at a plurality of distributed locations within a receptacle of the handle portion that is configured to accommodate a digit of a user's hand, wherein the plurality of distributed locations surround the digit of the user's hand when inserted therein.

10. The surgical tool of claim 9, wherein a position of each of the plurality of distributed locations within the receptacle corresponds to a location of a respective means for sensing a property of the patient.

11. The surgical tool of claim 9, wherein the receptacle is configured to accommodate the user's thumb.

12. A method comprising:
sensing a property with a sensor disposed at a distal end of a tool;
determining a direction of orientation of the sensor configured to sense the property; and
activating one or more of a plurality of haptic actuating devices positioned in a receptacle of a handle of the tool whereby the one or more of a plurality of haptic actuating devices that are being activated are positioned in the receptacle in a location corresponding to the direction of orientation of the sensor,
wherein the one or more of a plurality of haptic actuating devices are activated to impose a haptic effect on one or more digits of a user's hand positioned within the receptacle, and
wherein the plurality of haptic actuating devices are positioned in the receptacle to surround one or more digits of a user's hand positioned therein.

\* \* \* \* \*